United States Patent
Zygmunt et al.

(10) Patent No.: US 12,350,252 B2
(45) Date of Patent: Jul. 8, 2025

(54) WATER-SOLUBLE CANNABINOID FORMULATIONS AND METHODS OF THEIR MAKING

(71) Applicant: SOLUSCIENCE, LLC, Lafayette, CO (US)

(72) Inventors: Jan Zygmunt, Longmont, CO (US); Thomas Blakeley, Boulder, CO (US); Jesse G. Brown, Thornton, CO (US)

(73) Assignee: SOLUSCIENCE, LLC, Lafayette, CO (US)

( * ) Notice: Subject to any disclaimer, the term of this patent is extended or adjusted under 35 U.S.C. 154(b) by 545 days.

(21) Appl. No.: 17/425,630

(22) PCT Filed: Dec. 31, 2020

(86) PCT No.: PCT/US2020/067726
§ 371 (c)(1),
(2) Date: Jul. 23, 2021

(87) PCT Pub. No.: WO2021/138597
PCT Pub. Date: Jul. 8, 2021

(65) Prior Publication Data
US 2022/0142969 A1    May 12, 2022

Related U.S. Application Data

(60) Provisional application No. 62/956,103, filed on Dec. 31, 2019.

(51) Int. Cl.
*A61K 31/352* (2006.01)
*A61K 9/107* (2006.01)
(Continued)

(52) U.S. Cl.
CPC .......... *A61K 31/352* (2013.01); *A61K 9/107* (2013.01); *A61K 31/05* (2013.01); *A61K 45/06* (2013.01)

(58) Field of Classification Search
CPC ...... A61K 31/352; A61K 9/107; A61K 31/05; A61K 45/06; A61K 31/192; A61K 47/34; A61K 31/375; A61K 2300/00
See application file for complete search history.

(56) References Cited

U.S. PATENT DOCUMENTS

| | | |
|---|---|---|
| 10,265,293 B2 | 4/2019 | Goskonda et al. |
| 10,568,865 B2 | 2/2020 | Levy |

(Continued)

FOREIGN PATENT DOCUMENTS

| | | | |
|---|---|---|---|
| WO | WO 2012033478 A1 | 3/2012 | |
| WO | WO-2013149323 A1 * | 10/2013 | ............... A61K 8/42 |

(Continued)

OTHER PUBLICATIONS

Savjani KT, Gajjar AK, Savjani JK. Drug solubility: importance and enhancement techniques. ISRN Pharm. 2012;2012:195727. doi:10.5402/2012/195727. Epub Jul. 5, 2012. PMID: 22830056; PMCID: PMC3399483. (Year: 2012).*

(Continued)

*Primary Examiner* — Trevor Love
*Assistant Examiner* — Janet Joseph
(74) *Attorney, Agent, or Firm* — Cozen O'Connor

(57) ABSTRACT

The present invention discloses the water-soluble cannabinoid-containing solid dispersion and method of preparation thereof. The solid dispersion of the invention comprises one or more cannabinoids as active ingredients, a hydrophilic polymeric carrier, an antioxidant and optionally the palatability-improving agent. The solid dispersion is suitable for oral delivery application in form of solid material or an aqueous colloidal dispersion or for transdermal delivery application.

29 Claims, 1 Drawing Sheet

(51) Int. Cl.
*A61K 31/05* (2006.01)
*A61K 31/192* (2006.01)
*A61K 31/375* (2006.01)
*A61K 45/06* (2006.01)
*A61K 47/34* (2017.01)

(56) References Cited

U.S. PATENT DOCUMENTS

| | | | |
|---|---|---|---|
| 10,596,124 | B2 | 3/2020 | Kaufman |
| 10,709,747 | B2 | 7/2020 | Salm et al. |
| 10,722,490 | B2 | 7/2020 | Levy |
| 10,842,773 | B2 | 11/2020 | Levy |
| 2008/0069871 | A1* | 3/2008 | Vaughn .............. A61K 9/2013 424/456 |
| 2010/0273895 | A1* | 10/2010 | Stinchcomb .......... A61P 19/02 514/733 |
| 2011/0038930 | A1 | 2/2011 | Barnscheid et al. |
| 2013/0045314 | A1* | 2/2013 | Shastri ................ A23L 27/37 426/330 |
| 2015/0297556 | A1* | 10/2015 | Smith .................. A61K 47/08 424/449 |
| 2016/0008297 | A1* | 1/2016 | Schmaus ............... A61Q 19/02 424/59 |
| 2016/0184258 | A1 | 6/2016 | Murty et al. |
| 2016/0213624 | A1 | 7/2016 | Lindeman |
| 2016/0250178 | A1 | 9/2016 | Chen et al. |
| 2018/0353558 | A1* | 12/2018 | Kuhrts ................ A61K 9/0014 |
| 2018/0360704 | A1* | 12/2018 | Riefler ................ A61K 36/06 |
| 2019/0015383 | A1 | 1/2019 | Woelfel et al. |
| 2019/0030170 | A1 | 1/2019 | Kingsley et al. |
| 2019/0167583 | A1 | 6/2019 | Shah |
| 2019/0183853 | A1 | 6/2019 | Levy |
| 2019/0201350 | A1* | 7/2019 | White ................. A61K 31/525 |
| 2019/0365667 | A1 | 12/2019 | Wright et al. |
| 2020/0121637 | A1 | 4/2020 | Levy |
| 2020/0170944 | A1 | 6/2020 | Jackowetz et al. |
| 2020/0222360 | A1* | 7/2020 | Knöller ............... A61K 9/1075 |
| 2020/0297690 | A1 | 9/2020 | Crary |

FOREIGN PATENT DOCUMENTS

| | | | |
|---|---|---|---|
| WO | WO 2015184127 A2 | 12/2015 | |
| WO | WO-2016027259 A1 * | 2/2016 | ............. A61K 31/05 |
| WO | WO 2019008178 A1 | 1/2019 | |
| WO | WO 2019135077 A1 | 7/2019 | |
| WO | WO-2019159174 A1 * | 8/2019 | ............. A61K 31/05 |

OTHER PUBLICATIONS

Ajjarapu et al. Melt Fusion Techniques for Solubility Enhancement: A Comparison of Hot Melt Extrusion and KinetiSol® Technologies. Scientia Pharmaceutica. 2022; 90(3):51. https://doi.org/10.3390/scipharm90030051 (Year: 2022).*

PCT/US2020/067726 International Search Report and Written Opinion dated Mar. 25, 2021, 11 pages.

* cited by examiner

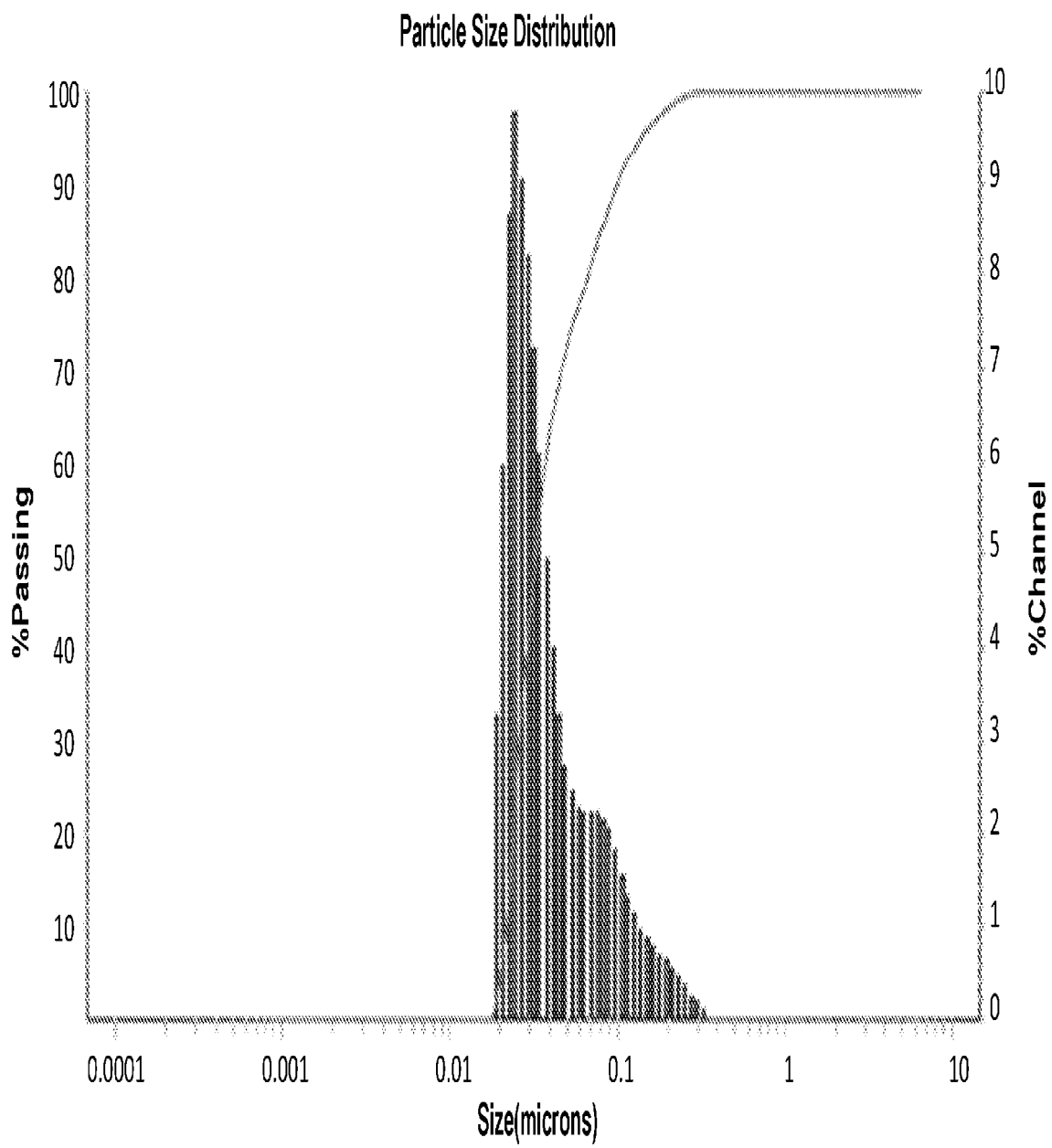

WATER-SOLUBLE CANNABINOID FORMULATIONS AND METHODS OF THEIR MAKING

CROSS-REFERENCE TO RELATED APPLICATION

This application claims benefit of priority to U.S. Provisional Patent Application No. 62/956,103 filed on Dec. 31, 2019, which is incorporated herein by reference in its entirety.

FIELD OF THE INVENTION

The present invention relates to the solid, water-soluble cannabinoid formulation compromising pharmaceutically acceptable water-soluble polymeric matrix and antioxidant agent, which after contact with water forms stable aqueous solution of highly bioavailable cannabinoid with improved in vivo absorption profile and faster onset when compared to the oil-based formulations.

BACKGROUND

Cannabinoids are hydrophobic molecules practically insoluble in water. As a result of this insolubility, the bioavailability of cannabinoids is a limited and their application in medicine is a major challenge, particularly if the treatment requires relatively high dosage.

A limited number of cannabinoid formulations are currently available on the market. To overcome insolubility challenge of cannabinoids vegetable oils, alcohol and propylene glycol are used as dissolving media. But these cannabinoid solutions have limited bioavailability and stability and often cause gastrointestinal side effects. For example, Epidiolex, which is delivered orally contains cannabidiol dissolved in sesame oil and up to 10% v/v of ethanol. Marinol, which is delivered in form of capsules, includes a solution of synthetic tetrahydrocannabinol in sesame oil. Sativex, which is delivered as a liquid by spray, includes solution of an equal combination tetrahydrocannabinol and cannabidiol in ethanol and propylene glycol.

Several alternative cannabinoid formulations have been described in the patent literature. U.S. Pat. No. 10,265,293 discloses an aqueous-based oral formulation of synthetic tetrahydrocannabinol comprising propylene glycol, polyethylene glycol ethanol and water.

WO 2019135077 discloses oral formulation for a combination of two cannabinoids, which compromises an organic solvent such as propylene glycol, propylene glycol diacetate, triacetin present from 20 to 50% and hydrophilic surfactants such as poloxamers.

U.S. Pat. Nos. 10,568,865, 10,722,490, 10,842,773 and US20200121637 describe water-soluble formulation, wherein cannabinoid, Vitamin E TPGS and water were mixed and then sonicated. The liquid formulation was transformed to solid after removal of water under low pressure. Vitamin E TPGS excipient and sonication there are factors, which can significantly contribute to the high cost of the process if it is scaled up. Water removal to get solid form of the formulation is another high cost step.

US 20200222360 discloses water-soluble formulation of cannabinoids formed from tocopherol (Vitamin E), poloxamer, glycerol, carboxylic acid and water.

WO 2012/033478 discloses water-soluble formulation of cannabinoids based on Self Emulsifying Drug Delivery Systems (SEDDS). This formulation compromises gliceride-based oil, which dissolves cannabinoids, one or more lipid-based surfactants, which promote self-emulsification and co-solvent enhancing stability of an emulsion. When in contact with gastric fluids, this system emulsifies because of the presence of surfactants. Most surfactants, co-surfactants and all oil carriers included in the self-emulsifying formulations are lipid-based excipients. They lose part of their emulsification capability in gastro-intestinal track because of interaction with lipase enzymes what results in decrease of bioavailability of applied cannabinoids. In addition, the high concentrations of surfactants and oil-based carriers, which is required to keep the formulation stable, causes several gastrointestinal unwanted side effects. Presence of water miscible co-solvents, which is also needed to help in stability of emulsions, is a challenge as well because these excipients can be toxic to the human body. To properly homogenize self-emulsifying formulations expensive high shear mixers are needed what significantly can increase the cost of production on bigger scale.

Despite these disadvantages, self-emulsifying formulations of cannabinoids are promoted in several other patents.

U.S. Pat. No. 10,596,124 discloses lipid-based formulation for cannabinoids compromising liquid lipid like medium chain triglicerides, soya lecithin, polysorbate 80, which dissolve cannabinoid and phospholipid such as phosphatidylcholine that encapsulate the lipid solution droplets.

US 20200170944 describes water-soluble emulsifying composition comprising cannabinoid, carrier oil based on glycerin and fatty acid monoester and emulsifier, which is sucrose fatty acid monoester or lecithin.

US 20190015383 describes water-soluble emulsifying composition including cannabinoid, carrier oil, water and polymeric carbohydrates such as starch, maltodextrin or sugar alcohol.

U.S. Pat. No. 10,709,747 discloses formulation, which uses emulsification process to encapsulate cannabinoids and includes blend of two or more surfactants where at least one surfactant is an oil carrier and the other form self-assembling emulsion, and hydrophilic co-solvent including alcohols, glycols and others.

US 20160184258 describes self-emulsifying formulation of *Cannabis* extract comprises gliceride-based or free fatty acids oil, one or more lipid-based surfactants and co-solvent ethanol.

US 20160213624 describes formulations of hemp oil by emulsification with a surfactant/emulsifier Polysorbate 80.

WO 2015/184127 discloses formulation of synthetic tetrahydrocannabinol, Drobinol using vegetable oils and different glicerides and ethanol; the patent reveals also formulation of Drobinol based on a mix of polyethylene glycol and propylene glycol and optionally water.

WO 20190167583 described oral cannabinoid formulation including a lipid solvent, a sweetener and ethanol.

US 20200297690 describes composition of water-soluble powder comprising cannabinoid, phospholipids or glicerides, sugar alcohols such as xylitol or mannitol, polysaccharide maltodextrin and amino acids.

US 20190365667 describes an oral cannabinoid formulation comprising one or more cannabinoids dissolved in a solvent system consisting of water and non-ionic surfactant such as Polysorbate 80, Kolliphor® RH40, polyoxyethylene or poloxamers. Preferred non-ionic surfactant is Kremophor® RH 40, which is derivative of hydrogenated castor oil and ethylene oxide.

US 20190030170 describes a water-soluble cannabinoid formulation based on inclusion complex of cannabinoid with sulfobuty ether of beta cyclodextrin, Captisol. However, Captisol is synthetic high-cost cyclodextrin and the scale-up production of the complex may not be economically viable.

One objective of the present invention is to develop an alternative water-based formulation of cannabinoids with a better pharmaceutical profile than formulations based on co-solvents and lipid-based oil carriers and surfactants.

Another objective of the present invention is to develop formulation, which can deliver orally an efficient amount of cannabinoid such that a 10 mL volume of the formulation in a liquid oral form includes 50 mg-100 mg of an active cannabinoid or more.

Another objective of the present invention was to develop solid and stable cannabinoid formulation, which can be applied in the form of a solid dosage (in statu nascendi oral formulation) or can be dissolved in an aqueous medium to generate the oral solution of an active cannabinoid at desired concentration.

Another objective of the present invention was to develop solid active formulation including an active cannabinoid, which can be conveniently applied by oral administration or via other delivery routes such as transdermal, topical, sublingual or others routes used for pharmaceutical delivery.

SUMMARY

This disclosure provides the next generation of water-soluble cannabinoid formulation based on solid dispersion. In one embodiment, the formulation has increased efficacy and the superior bioavailability characteristics in comparison to other cannabinoid formulations based on lipids.

According to the present disclosure, a water-soluble solid dispersion formulation is provided. In one embodiment, the formulation comprises one or more cannabinoids dispersed in a pharmaceutically acceptable hydrophilic polymeric matrix and an antioxidant component, which ensures stability of the cannabinoids.

In another embodiment, the solid dispersion formulation according to the present disclosure may contain a mixture of cannabinoids with one or more terpenoids or other biologically active compounds.

In another embodiment, the solid dispersion formulation can be applied in solid, liquid or gel form and delivered orally, sublingually or transdermally.

In one aspect, the polymeric matrix may be selected from the group of amphiphilic polymers such as poloxamers. In another aspect, the polymeric matrix is Poloxamer 407. Poloxamer 407 is tri-block polymer built from polyoxyethylene and polyoxypropylene blocks. It is soluble in water and approved by FDA to use in humans. In another aspect, the hydrophilic polymeric matrix is present from 70% to 95% by weight of the solid dispersion formulation.

In another embodiment, the cannabinoid material is present from 5% to 30% by weight of the solid dispersion formulation. In another embodiment, the disclosed method comprises a process of hot-melt fusion, spray drying or hot melt extrusion. In one aspect, the disclosed method comprises a process of hot-melt fusion (HMF). In one aspect, the one or more cannabinoids are phytocannabinoids or synthetic cannabinoids. The cannabinoid material can be in the form of a liquid obtained by extraction from plant and purified by vacuum distillation or in the form of solid isolate purified by chromatography and crystallization. In another aspect, examples of the one or more cannabinoids included in the cannabinoid material may include but are not limited to: cannabichromene (CBC), cannabichromenic acid (CBCV), cannabidiol (CBD), cannabidiolic acid (CBDA), cannabidivarin (CBDV), cannabigerol (CBG), cannabigerol propyl variant (CBGV), cannabicyclol (CBL), cannabinol (CBN), cannabinol propyl variant (CBNV), cannabitriol (CBO), tetrahydrocannabinol (THC), tetrahydrocannabinolic acid (THCA), tetrahydrocannabivarin (THCV) or tetrahydrocannabivarinic acid (THCVA). In another aspect, the one or more cannabinoids are cannabidiol (CBD), cannabinol (CBN) or cannabigerol (CBG).

In another embodiment, the cannabinoid material may be combined with other biologically active substances. In one aspect, the biological active substance can include terpenoids, retinol and retinol derivatives and others. In another aspect, the ratio of the cannabinoid material to polymeric matrix is used from 1:3 to 1:6 and more preferably is 1:4 by weight.

In another embodiment, the antioxidant is selected from the group consisting ascorbic acid, ascorbyl palmitate, alpha-tocopherol, butylated hydroxytoluene, butylated hydroxyanisole, propyl gallate, sodium sulphite, sodium metabisulphite, sodium formaldehyde sulphoxylate and mixtures thereof. In another embodiment, the antioxidant is present from 0.1% to 10%, from 0.2% to 2%, 0.4% to 0.6%, or 0.5% by weight of the solid dispersion formulation. In another embodiment, the antioxidant is ascorbic acid, which is approved by FDA to use in pharmaceutical formulations and food industry.

In another embodiment, the solid dispersion formulation according to the present disclosure may additionally contain a taste-masking agent. In one aspect, by way of example, the taste-masking agent may be a vegetable glycerin. In another aspect, the vegetable glycerin is present from 0.1% to 5%, 0.5% to 3%, 1% to 2%, or 1.5% by weight of the solid dispersion formulation. Glycerin is pharmaceutical excipient accepted for oral use IID limit of 500 mg/mL.

In a further embodiment, the cannabinoid material of the solid dispersion formulation includes 50% of cannabidiol, 25% of cannabigerol and 25% of cannabinol by weight of the solid dispersion.

In a further embodiment, the disclosed solid dispersion formulation when in contact with water converts to the colloidal dispersion formulation where cannabinoid molecules are encapsulated and the diameter of the resulting micelles is smaller than 100 nanometers.

In a further embodiment, the colloidal dispersion formulation may further contain one or more of the following: an antifoaming agent, a test-masking agent, a preservative, a flavoring agent, or a sweetener.

In a further embodiment, the colloidal dispersion contains an antifoaming agent. By way of example, the antifoaming agent may be silicone-based food acceptable agent. In another aspect, the silicone-based food acceptable agent is present at a concentration of not more than 10 ppm by weight of the formulation.

In a further embodiment, the colloidal dispersion further contains one or more preservatives, wherein the one or more preservatives are selected from one or more of the following: potassium sorbate, sodium benzoate, methyl parahydroxybenzoate, ethyl para-hydroxybenzoate, propyl para-hydroxybenzoate or butyl para-hydroxybenzoate. In another aspect, the one or more preservatives include a combination of potassium sorbate and sodium benzoate in equal amounts of 0.1% each by weight of the formulation.

In a further embodiment, the colloidal dispersion further contains flavoring, which is selected from: blackcurrant, orange, spearmint and peppermint flavoring agents at a concentration of 0.001% to 1% by weight of the formulation. In one aspect, the flavoring agent is spearmint-flavoring agent and is at a concentration of 0.1%-2%, 0.2%-1%, 0.4%-0.6%, or 0.5% by weight of the formulation. Peppermint oil is commonly used as a flavoring in oral medications and dietary supplements (IID limits of 100 mg/mL).

In a further embodiment, the colloidal dispersion further contains a sweetener. In one aspect, the sweetener is glucose at a concentration of 0.1%-2%, 0.2%-1%, 0.4%-0.6%, or 0.5% by weight of the formulation.

In one embodiment, for 2% of CBD in aqueous solution, the amount of polymer matrix required to form a homogenic and stable colloidal dispersion is around 80 mg/mL.

In a further embodiment, the solid dispersion formulation may be mixed with cosmetic components designed to moisturize skin and help penetration of formulated cannabinoid into or through the skin and is in the form of a serum, an ointment, a cream, an emulsion, a lotion, a paste, an unguent, a gel or a sunscreen. The solid dispersion may include the cannabinoid material only or it may include the cannabinoid material mixed with a combination of retinol and retinol acetate wherein the ratio between retinol and retinol acetate is between 2:1 and 1:2 or about 1:1 by weight.

In another aspect of the present disclosure, a method of preparing a solid dispersion formulation of cannabinoid is provided. In one embodiment, the method may include the steps of:
i) preparing a solid dispersion of cannabinoid material and pharmaceutically acceptable hydrophilic polymeric matrix by homogenization at the elevated temperature including antioxidant and taste-masking agent, and
ii) cooling the resulting melt and grinded to form an oral solid dispersion cannabinoid containing oral formulation.

In one aspect, the solid dispersion formulation can be used in a solid form of capsules, tablets and other solid drug delivery method.

In another aspect, the solid dispersion formulation can be used in form of colloidal dispersion formulation after dissolving it in water comprising the steps of:
i) preparing a solid dispersion of cannabinoid material and pharmaceutically acceptable hydrophilic polymeric matrix by homogenization at the elevated temperature including antioxidant and taste-masking agent,
ii) adding a proper amount of water and homogenize to the liquid concentrate, and
iii) adding soluble excipients including an antifoaming agent, preservatives and a flavoring and homogenize.

In one embodiment, the formulation is aseptically filled into a bottle or other container.

BRIEF DESCRIPTION OF THE DRAWINGS

FIG. 1 demonstrates the particle size distribution. The average size of the particles was found to be 32 nm. Such particle size is vital to get high bioavailability and make possible fast uptake of the active agent into the blood and then to cells.

DETAILED DESCRIPTION

Method of Manufacture

According to one embodiment of the present disclosure, the solid dispersion formulation of cannabinoid is prepared as per the following steps:
1) stir Poloxamer 407 and ascorbic acid under heat to get the liquid melt,
2) add the cannabinoid material and glycerin to it and stir well to homogenize,
3) cool the liquid and grind the resulting solid dispersion, and
4) fill the resulting flakes into a proper container.

According to one embodiment of the present disclosure, the colloidal dispersion formulation of cannabinoid is prepared as per the following steps:
1) stir Poloxamer 407 and ascorbic acid under heat to get the liquid melt,
2) add the cannabinoid material and glycerin to it and stir well to homogenize,
3) add an appropriate amount of water to it and stir until full homogenization,
4) add an antifoaming agent, preservatives and a flavoring and stir well to homogenize, and
5) filter and fill the resulting homogenic colloidal dispersion into a bottle or other container.

Bioavailability

The obtained cannabinoid solid dispersion formulations were preliminary tested in a form of colloidal dispersion formulation by volunteers to determine if they are safe and effective. The tested solutions showed the fast onset of the expected physiological effects and no safety concerns were noticed. This preliminary data have significant importance because they showed for the first time that such cannabinoid solid dispersion formulation of the present invention is able to improve significantly the bioavailability of CBD and other cannabinoids and mixture of them. And at the same time this solid formulation provides stable and palatable product in comparison to lipid-based formulations.

Antioxidants

Most of cannabinoids are prone to oxidize because their molecules include phenolic ring, which in the presence of air and light easy undergoes oxidation to quinones. This oxidation is even more intensive when cannabinoids molecules are in dispersed stage. Because quinones are colorful cannabinoid products changes overtime their color from white to yellow to dark blue what indicates degradation of the initial product and its contamination with foreign chemicals. To stop cannabinoids oxidative degradation the antioxidants need to be included in cannabinoids formulations.

The following antioxidants agents were screened for use within the solid formulation: ascorbic acid, Vitamin E, ascorbyl palmitate, butylated hydroxytoluene (BHT) and butylated hydroxyanisole (BHA).

According to one embodiment of the present disclosure, ascorbic acid is chosen as the best option to eliminate oxidation in the solid phase as well as in aqueous solutions.

Taste Masking

Cannabinoids when solubilized in aqueous phase and taken orally produce a burning sensation in the mouth. They also interact with the *capsicum* receptors within the mouth what results in throat catch commonly associated with smoking cigarettes.

Surfactant used for solubilization can also generate bitter taste with an unlikable lingering of the bitterness. According to one embodiment of the present disclosure, it is important to optimize the taste of the colloidal dispersions of the cannabinoid solid dispersion formulation disclosed in the present disclosure.

To mask the bitterness and the burning sensation that the surfactant and cannabinoids produced two basic taste-masking agents such as vegetable glycerin and Vitamin E and several flavors were tested.

The flavors may be added to the aqueous solution of the solid dispersion formulation and blackcurrant, orange, spearmint and peppermint flavoring agents. According to one embodiment of the present disclosure, of these flavors, the spearmint-flavoring agent demonstrated satisfied result.

Combination of vegetable glycerin and spearmint oil was chosen as the best option to reduce bitterness and burning of the colloidal dispersions disclosed in the present invention containing cannabinoids such as CBD, CBG, CBN, THC and mixtures of them.

Preservatives

To protect oral liquids against grow of microorganisms, mold, and fungus the presence of specific preservatives is required. Aqueous solutions of the cannabinoid solid dispersion formulation disclosed in the present invention are example of the oral liquids and to maintain their microbiological quality they need to contain these preservatives.

The most widely used preservatives are potassium sorbate, sodium benzoate and esters of 4-hydroxybenzoic acid called parabens approved by FDA as inactive ingredients.

Usually more than one paraben is used because they act better in combination. Example is a mixture of methyl, ethyl and propyl parabens, which shows enhanced antimicrobial properties versus the individual components. Propyl parabens is the most active however, it has the lowest solubility in aqueous phase because increased hydrophobicity and its activity is reduced in the presence of non-ionic surfactant because of micellization.

According to one embodiment of the present disclosure, to maintain microbiological quality of the colloidal dispersions of the cannabinoid solid dispersion formulation disclosed in the present invention the following preservatives were tested: potassium sorbate, sodium benzoate, methyl paraben and propyl paraben.

The mixture of potassium sorbate and sodium benzoate in equal amounts present in an amount of 0.1% each by weight of the formulation was chosen as the best option to control microbiological quality of the colloidal dispersions disclosed in the present invention.

Stability Study

The solid dispersion included 20% CBD, 75% of Poloxamer 407 and 5% ascorbic acid was dissolved in distilled water to produce the homogenic, stable colloidal dispersion of cannabidiol at 2% (20 mg/mL) by weight of the formulation. The formulation was tested in accelerated stability study and the obtained analytical data are showed in Table 1. The obtained results revealed that over a period of 90 days (3 months) at 38° C. of accelerated stability study, an equivalent to 12 months at ambient temperature, there was practically no change in CBD content.

No turbidity, no precipitation of solid or emulsion and no change of the pH value of the solution were observed. No grow of yeast and mold has been observed in the tested sample either. The only major change was the appearance of the solution turning yellow/slight brown.

For purpose of this disclosure, a full-spectrum cannabinoid distillate contains CBD and one or more naturally occurring *Cannabis* plant extracts such as other cannabinoids, terpenes and flavonoids. A full-spectrum cannabinoid distillate typically includes from 0.001% to 0.3% (w/w) THC, but not more than 0.3% (w/w) THC; a broad-spectrum cannabinoid distillate contains CBD and other cannabinoids, terpenes and flavonoids as well but a broad-spectrum cannabinoid distillate is entirely free of THC; a cannabinoid isolate includes only pure CBD (i.e., greater than 99.9% CBD).

The term "solid dispersion" refers to a solid product containing at least two different components, typically a hydrophilic matrix and a hydrophobic ingredient. In general, solid dispersion is defined as the dispersion of one or more active ingredient in a carrier or matrix at a solid state.

TABLE 1

CANNABINOID PROFILE
Accelerated stability test: the samples were stored at 100° F. (38° C.) for 90 days what is equivalent to 360 days at ambient temperatures.

| Compound | LOQ (%) | Result (%) | Result (mg/g) |
|---|---|---|---|
| Day # 0; sample - colorless, homogenous colloidal dispersion | | | |
| Delta 9-Tetrahydrocannabinolic acid (THCA-A) | 0.04 | ND | ND |
| Delta 9-Tetrahydrocannabinol (Delta 9THC) | 0.02 | ND | ND |
| Cannabidiolic acid (CBDA) | 0.05 | ND | ND |
| Cannabidiol (CBD) | 0.03 | 2.02 | 20.2 |
| Delta 8-Tetrahydrocannabinol (Delta 8THC) | 0.02 | ND | ND |
| Cannabinolic Acid (CBNA) | 0.05 | ND | ND |
| Cannabinol (CBN) | 0.02 | 0.03 | 0.3 |
| Cannabigerolic acid (CBGA) | 0.03 | ND | ND |
| Cannabigerol (CBG) | 0.02 | 0.03 | 0.3 |
| Tetrahydrocannabivarinic Acid (THCVA) | 0.03 | ND | ND |
| Tetrahydrocannabivarin (THCV) | 0.02 | ND | ND |
| Cannabidivarinic Acid (CBDVA) | 0.05 | ND | ND |
| Cannabidivarin (CBDV) | 0.03 | ND | ND |
| Cannabichromenic Acid (CBCA) | 0.03 | ND | ND |
| Cannabichromene (CBC) | 0.03 | ND | ND |
| Total Cannabinoids | | 2.08 | 20.80 |
| Total Potential THC** | | ND | ND |
| Total Potential CBD** | | 2.02 | 20.20 |
| Day # 90; sample - yellow/light brown, homogenous colloidal dispersion | | | |
| Delta 9-Tetrahydrocannabinolic acid (THCA-A) | 0.07 | ND | ND |
| Delta 9-Tetrahydrocannabinol (Delta 9THC) | 0.03 | ND | ND |
| Cannabidiolic acid (CBDA) | 0.02 | ND | ND |
| Cannabidiol (CBD) | 0.05 | 2.19 | 21.9 |
| Delta 8-Tetrahydrocannabinol (Delta 8THC) | 0.04 | ND | ND |
| Cannabinolic Acid (CBNA) | 0.09 | ND | ND |
| Cannabinol (CBN) | 0.04 | ND | ND |
| Cannabigerolic acid (CBGA) | 0.06 | ND | ND |
| Cannabigerol (CBG) | 0.03 | ND | ND |
| Tetrahydrocannabivarinic Acid (THCVA) | 0.08 | ND | ND |
| Tetrahydrocannabivarin (THCV) | 0.03 | ND | ND |
| Cannabidivarinic Acid (CBDVA) | 0.02 | ND | ND |
| Cannabidivarin (CBDV) | 0.01 | ND | ND |
| Cannabichromeric Acid (CBCA) | 0.05 | ND | ND |
| Cannabichromene (CBC) | 0.06 | ND | ND |
| Total Cannabinoids | | 2.19 | 21.9 |
| Total Potential THC** | | ND | ND |
| Total Potential CBD** | | 2.19 | 21.9 |

Particle Size

The solid dispersion included 20% CBD, 75% of Poloxamer 407 and 5% ascorbic acid was dissolved in distilled water to produce the homogenic, stable colloidal dispersion of cannabidiol at 2% (20 mg/mL) by weight of the formulation. The dispersion was tested on a Microtrac Dynamic Light Scattering instrument in order to measure the particle size of the micelles produced by the formulation.

FIG. 1 demonstrates the particle size distribution. The average size of the particles was found to be 32 nm. Such particle size is vital to get high bioavailability and make possible fast uptake of the active agent into the blood and then to cells.

The disclosure will now be illustrated with working examples, and which is intended to illustrate the working of disclosure and not intended to restrictively any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

EXAMPLES

Example 1: Preparation of 20% Cannabidiol Flakes (Small Scale)

7.500 g of Poloxamer 407 ingredient was placed in a 250 mL RBF equipped with a magnetic stirring bar and the flask was loosely closed with a septum and then placed in a preheated ~80° C. oil bath. Poloxamer 407 slowly melted over 7 min and the resulting milky liquid was stirred at ~80° C. for 10 min. Then 0.502 g of ascorbic acid was added and the resulting liquid was stirred for 10 min at the same temp. Then 2.011 g of cannabinoid was added and the milky liquid is stirred vigorously at ~80°-81° C. for 15 min. The flask is removed from the oil bath and cooled down in $CO_2$/acetone bath for 30 min and then warmed up to room temperature. The resulting white solid was transferred to a glass vial by spatula: m=9.76 g.

Example 2: Preparation of 20% Cannabidiol Flakes (Scale-Up)

In a 20 L reactor preheated to 80° C. was placed 937.5 g of Poloxamer 407 ingredient and stirred at 100 RPM over 20 minutes until full melting was achieved. To the resulting melt was added 937.5 g of Poloxamer 407 and the liquid was stirred for 20 minutes. Then 125 g of ascorbic acid was added in one portion and the resulting liquid mixture was stirred for 10 min at the same RPM. Then 250 g of cannabinoid was added and after 20 min stirring the second 250 g portion of cannabinoid was added and the resulting liquid mixture was stirred for 1.5 h at 200 RPM. The liquid was removed from the reactor and cooled at −20° C. overnight. The resulting solid was shredded to produces a white flake; yield 95% (by mass).

Example 3 Preparation of the Colloidal Dispersion Solution of 53 mg CBD/L

To magnetically stirred at room temperature 500 mL of distilled water was added 132.2 mg of 20% cannabidiol flakes and the heterogenic mixture was stirred for 1 hour to yield homogenic, transparent colloidal dispersion.

Example 4 Preparation of the Colloidal Dispersion Concentrate of 40.1 g CBD/L 100 mL measuring cylinder was filled up with distilled water to 20 mL. The magnetic stir bar was added and the water volume increased to 22 mL. Then 5.015 g of 20% CBD was added and the heterogenic mixture volume was increased to 27 mL. The mixture was first gently agitated manually with spatula. Then the cylinder was closed with parafilm and the heterogenic mixture was stirred overnight to give 25 mL of homogenic, dense and partially transparent colloidal dispersion. 1 drop (~0.05 mL) of the solution includes 2.0 mg CBD.

Example 5 Preparation of 20% Flakes from the Crude Mixture of CBN and CBD

Starting material: brown viscous oil, mixture of 64.0% CBN, 6.6% CBD, 0.2% THC; 29.2%=wax, fatty acids and other organic material.

In 250 mL RBF equipped with magnetic stirring bar was placed 2.005 g of the CBN/CBD mixture, 7.503 g of Poloxamer 407 and 0.503 g of ascorbic acid. The flask was closed loosely with septum and placed in preheated to ~80° C. oil bath. The mixture was slowly melted and equitable stirring was achieved after 10 min at ~80° C. and then the resulting light brown milky liquid was intensively stirred at same temperature for 15 min. The flask was removed from oil bath, closed tightly with a septum, cooled down in $CO_2$/acetone bath for 1 h. Then the flask was warmed up to RT and the resulting light brown partially waxy solid was transferred to a glass vial using spatula: m=9.67 g.

Example 6 Preparation of the Colloidal Dispersion of 20 g CBN/CBD Mix/L

In 30 mL glass vial was weighted 10.0 g of distilled water (=10.0 mL). The level of water was carefully marked and the vial was empted and dried. Then 1.004 g of 20% CBN/CBD mix flakes was placed in the vial and then water was added to the marked level. The resulting heterogenic mixture was stirred manually with glass road for few minutes and then a magnetic stir bar was added and the partially heterogenic mixture was stirred overnight to give a homogenic light brown transparent viscous liquid. 1 drop (~0.05 mL) of the solution includes 1.0 mg of CBN/CBD mix=0.64 mg of CBN, 0.07 mg CBD and 0.002 mg THC.

Example 7 One-Step Preparation of the Colloidal Dispersion of 20 g CBN/CBD Mix/L In 250 mL RBF equipped with magnetic stirring bar was placed 2.119 g of the CBN/CBD mixture, 7.949 g of Poloxamer 407 and 0.532 g of ascorbic acid. The flask was loosely closed with septum and immersed in preheated to ~80° C. oil bath. The mixture was slowly melted and equitable stirring was achieved after 5 min at ~82° C. and then the resulting light brown milky liquid was intensively stirred at 81°-82° C. for 15 min. Then the flask was removed from oil bath, closed tightly with a septum, cooled down in $CO_2$/acetone bath for 1 h and then warmed up to RT to get light brown solid. To the flask was added 98.10 g of water and the solid was slowly agitated manually by spatula to let water penetrate in (~30 min). The flask was closed with a septum and partially heterogeneous mixture was slowly stirred overnight to give the light yellow, homogenic and mostly transparent colloidal dispersion.

Example 8 Preparation of 20% CBD Melt and Conversion to the Flakes or the Colloidal Dispersion Concentrate (Scale Up)

In the stainless steel jacketed reactor was placed 3.84 kg of Poloxamer 407 and the polymer was slowly stirred at 80°-85° C. temperature (internal temperature) until it melted into a creamy paste. To the paste 0.15 kg glycerin was added and stirring was continued for 10 minutes and then 0.01 kg of ascorbic acid was added and the mixture was stirred for 20 minutes. After that 1 kg of cannabidiol isolate was added stepwise and the melt was stirred at 200 RPM for 1.5 hours.

Conversion to solid dispersion flakes: the melt was transferred to a tray, forming a thin layer and the tray was sealed and placed in a freezer at −20° C. overnight. The resulting solid cold slabs were grinded in a motorized grinder to make flakes. Yield 95%.

Conversion to colloidal dispersion liquid concentrate: heating was turned off and to the stirred melt 45 L of distilled water was added gradually and the heterogenic mixture was stirred slowly over a couple of hours then stirring was stopped and the resulting mixture was kept over 12 h at RT. Then slow stirring was initiated again for 1 hour and the resulting homogenic liquid was filtered to give a thick colloidal dispersion concentrate. Yield: 96%.

Example 9 One-Step Preparation of the CBD/Retinol/Retinol Acetate Colloidal Dispersion Concentrate (Scale-Up)

In the stainless steel jacketed reactor was placed 3.84 kg of Poloxamer 407 and the polymer was slowly stirred at 80°-85° C. temperature (internal temperature) until it melted into a creamy paste. To the paste 0.15 kg glycerin was added and stirring was continued for 10 minutes and then 0.01 kg of ascorbic acid was added and the mixture was stirred for 10 minutes. After that 1 kg of the mixture of CBD, retinol and retinol acetate comprising an equal mass amount of each component, was added stepwise and the melt was stirred at 200 RPM for a couple of hours. Then heating was turned off and to the stirred melt 20 L of distilled water was added gradually and the heterogenic mixture was stirred slowly over a couple of hours then stirring was stopped and the resulting mixture was kept over 12 h at RT. Then slow stirring was initiated again for 1 hour and the resulting homogenic liquid was filtered to give a thick colloidal dispersion concentrate. Yield: 95%.

Example 10 Preparation of 20% Cannabinoid Mixture Flakes Including CBD, CBN and CBG (Scale-Up)

In the stainless steel jacketed reactor was placed 3840 g of Poloxamer 407 and the polymer was slowly stirred at 800-85° C. temperature (internal temperature) over 30 min until it melted into a creamy paste. To that 1000 g of the pre-melted in an oven liquid cannabinoid material including 500 g CBD, 250 g of CBN and 250 g of CBG was added followed by 150 g of glycerin and 10 g of ascorbic acid and the resulting melt was stirred over 90 minutes. The melt was transferred to a tray and the tray was sealed and placed in a freezer at −20° C. overnight. The resulting cold slabs were broken to smaller pieces and grinded in a motorized grinder to make flakes. Yield 95%.

REFERENCES

The following references, patents or patent applications as well as all other references, patents or patent applications cited in this disclosure are incorporated herein in their entirety:
1. U.S. Pat. No. 10,265,293B2
2. WO2015184127A2
3. WO2012033478A1
4. US Appl. 0160213624
5. US20160184258A1
6. WO2019135077A1
7. US20190167583A1
8. U.S. Pat. No. 10,596,124B2
9. U.S. Pat. No. 10,709,747B2
10. U.S. Pat. No. 10,568,865B2
11. U.S. Pat. No. 10,722,490B2
12. U.S. Pat. No. 10,842,773B2
13. US20200121637A1
14. US20200222360A1
15. US20190030170A1
16. US20190015383A1
17. US20200170944A1
18. US20200297690A1
19. US20190365667A1

The invention claimed is:

1. A method of preparing a composition comprising a cannabinoid material, an antioxidant, and a pharmaceutically acceptable water-soluble polymer, wherein said cannabinoid material and antioxidant are dispersed in said water-soluble polymer in a jacketed reactor, and wherein the method comprises a hot-melt fusion process, said hot-melt fusion process taking place in a jacketed reactor.

2. The method of claim 1, wherein said composition is in a homogenous solid dispersion form or a homogenous aqueous micellar dispersion form.

3. The method of claim 1, wherein the composition further comprises a palatability-improving agent.

4. The method of claim 1, wherein said composition is capable of oral, sublingual, buccal or transdermal delivery to a subject.

5. The method of claim 1, wherein the cannabinoid material comprises one or more cannabinoids wherein the cannabinoid is selected from the group consisting of tetrahydrocannabinol, cannabidiol, cannabigerol, cannabigerolovarin, cannabichromene, cannabidivarin, tetrahydrocannabivarin, cannabivarin, cannabinol, and isomers thereof, and mixtures thereof.

6. The method of claim 1, wherein said cannabinoid material is extracted from a plant source and said cannabinoid material is selected from the group consisting of a full-spectrum cannabinoid distillate, a broad-spectrum cannabinoid distillate, a cannabinoid isolate, and cannabinoid crude oil.

7. The method of claim 1, wherein the cannabinoid material comprises one or more terpenoids selected from the group consisting of myrcene, limonene, linalool, caryophyllene, alpha-pinene and beta-pinene, alpha-bisabolol, eucalyptol, trans-nerolido, humulene, delta 3 carene, camphene, borneol, terpineol, valencene and geraniol and isomers thereof, and mixtures thereof.

8. The method of claim 1, wherein the composition further comprises one or more biologically active substances, said one or more biologically active substances being different from cannabinoid.

9. The method of claim 8, wherein the biologically active substance comprises retinol and retinol acetate at a weight ratio of about 1:1.

10. The method of claim 1, wherein the pharmaceutically acceptable water-soluble polymer is selected from the group consisting of polyvinylpyrrolidone, polyvinylpyrrolidone-polyvinylacetate copolymer, polyvinyl acetate phthalate, polyvinyl alcohol, polycaprolactam, polylactic acid, polyglycolic acid, polymethacrylic polymers, Poloxamers, polyvinyl acetate polyethylene glycol graft co-polymers, hydroxypropyl methyl cellulose phthalate, cellulose acetate phthalate, cellulose acetate trimellitate, cellulose acetate phthalate, methyl cellulose acetate phthalate, hydroxyethyl cellulose, hydroxypropyl cellulose, hydroxypropyl methylcellulose, hydroxypropyl cellulose acetate phthalate, cellulose acetate terephthalate, cellulose acetate isophthalate, hydroxypropyl methyl cellulose acetate succinate, hydroxypropyl methyl cellulose propionate succinate, carboxymethyl ethylcellulose, sodium carboxymethylcellulose, and mixtures thereof.

11. The method of claim 1, wherein the antioxidant is selected from the group consisting of ascorbic acid, ascorbyl palmitate, alpha-tocopherol, butylated hydroxytoluene, butylated hydroxyanisole, propyl gallate, sodium sulphite, sodium metabisulphite, sodium formaldehyde sulphoxylate and mixtures thereof.

12. The method of claim 1, wherein the cannabinoid material is present in an amount of 5% to 30% by weight of the composition, and wherein the pharmaceutically acceptable polymer is present in an amount of 70% to 95% by weight of the composition, and wherein the antioxidant is present in an amount of 0.1% to 10% by weight of the composition.

13. The method of claim 1, wherein the pharmaceutically acceptable water-soluble polymer belongs to poloxamers.

14. The method of claim 1, wherein the cannabinoid is cannabidiol, the water-soluble polymer is Poloxamer 407 and the antioxidant is ascorbic acid.

15. The method of claim 1, wherein the cannabinoid material comprises cannabidiol, cannabinol and cannabigerol, wherein cannabidiol is about 0% to 100% by weight of the cannabinoid material, cannabinol is about 0% to 100% by weight of the cannabinoid material and cannabigerol is about 0% to 100% by weight of the cannabinoid material.

16. The method of claim 1, wherein the composition is further made into a solid formulation in a form selected from the group consisting of tablets, granules, pellets, capsules and films.

17. The method of claim 2, wherein said composition is further made into a colloidal dispersion formulation by dissolving the solid dispersion formulation of claim 2 in water.

18. The method of claim 17, wherein the colloidal dispersion formulation further comprises one or more biological active compounds.

19. The method of claim 1, wherein the composition is further made into a gel formulation by dissolving the composition in water to form a gel.

20. The method according to claim 17, wherein the colloidal dispersion formulation further comprises an antifoaming agent, wherein the antifoaming agent is silicone-based food acceptable agent present at a concentration of not more than 10 ppm by weight of the formulation.

21. The method according to claim 17, wherein the colloidal dispersion formulation further comprises a flavoring agent at a concentration of 0.001% to 1% by weight of the formulation, wherein the flavoring agent is selected from the group consisting of blackcurrant, orange, spearmint, peppermint flavoring agent and combination thereof.

22. The method according to claim 21, wherein the flavoring agent is spearmint-flavoring agent present at a concentration of 0.5% by weight of the formulation.

23. The method according to claim 17, the colloidal dispersion formulation further comprising one or more preservatives and 1% by weight of sodium glutamate and 1% by weight of citric acid.

24. The method according to claim 23, wherein the one or more preservatives are selected from the group consisting of potassium sorbate, sodium benzoate, methyl para-hydroxybenzoate, ethyl para-hydroxybenzoate, propyl para-hydroxybenzoate and butyl para-hydroxybenzoate.

25. The method of claim 23, wherein the preservative is represented by combination of potassium sorbate and sodium benzoate in equal amount by weight.

26. The method according to claim 16, wherein the solid dispersion formulation is dissolved in water, the colloidal dispersion formulation comprising total cannabinoid material in amount of 2% by weight, citric acid and sodium gluconate in amount of 1% each by weight, potassium sorbate and sodium benzoate in an amount of 0.1% each by weight of the formulation.

27. A method of making a topical formulations comprising the composition of claim 1, wherein the composition of claim 1 is properly mixed with cosmetic components designed to moisturize skin and help penetration of formulated cannabinoid into or through the skin and is in the form of a serum, an ointment, a cream, an emulsion, a lotion, a paste, an unguent, a gel or a sunscreen.

28. The method of claim 9, wherein the composition of claim 9 is properly mixed with cosmetic components designed to moisturize skin and help penetration of formulated cannabinoid into or through the skin and is in the form of a serum, an ointment, a cream, an emulsion, a lotion, a paste, an unguent, a gel or a sunscreen.

29. The method of claim 1, further comprising a step of, after the cannabinoid material and antioxidant are dispersed in the water-soluble polymer to form a dispersion, adding water to the dispersion to form an aqueous micellar dispersion form.

* * * * *